US009671359B2

(12) United States Patent
Kotnala et al.

(10) Patent No.: US 9,671,359 B2
(45) Date of Patent: Jun. 6, 2017

(54) RESISTIVE TYPE HUMIDITY SENSOR BASED ON POROUS MAGNESIUM FERRITE PELLET

(71) Applicant: Council of Scientific & Industrial Research, Rafi Marg, New Delhi (IN)

(72) Inventors: Ravinder Kumar Kotnala, New Delhi (IN); Jyoti Shah, New Delhi (IN); Hari Kishan, New Delhi (IN); Bhikham Singh, New Delhi (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 412 days.

(21) Appl. No.: 14/466,723

(22) Filed: Aug. 22, 2014

(65) Prior Publication Data
US 2015/0061706 A1    Mar. 5, 2015

(30) Foreign Application Priority Data

Aug. 27, 2013  (IN) .................................. 2528/2013

(51) Int. Cl.
G01N 27/00 (2006.01)
G01N 27/12 (2006.01)
B23K 20/00 (2006.01)
C04B 38/00 (2006.01)
C04B 35/26 (2006.01)
C04B 35/626 (2006.01)
C04B 111/90 (2006.01)

(52) U.S. Cl.
CPC ......... *G01N 27/121* (2013.01); *B23K 20/004* (2013.01); *C04B 35/26* (2013.01); *C04B 35/6261* (2013.01); *C04B 35/62675* (2013.01); *C04B 35/62695* (2013.01); *C04B 38/009* (2013.01); *C04B 38/0038* (2013.01); *C04B 38/0051* (2013.01); *C04B 2111/90* (2013.01); *C04B 2235/3206* (2013.01); *C04B 2235/5445* (2013.01); *C04B 2235/5454* (2013.01); *C04B 2235/6562* (2013.01); *C04B 2235/6567* (2013.01); *C04B 2235/94* (2013.01); *C04B 2235/96* (2013.01)

(58) Field of Classification Search
CPC ..... C04B 35/26; C04B 35/64; C04B 35/2641; C04B 35/6261; C04B 35/62675; C04B 35/62695; C04B 38/009
USPC ..................... 423/138, 594.2; 338/35; 73/73; 324/694; 228/180.5; 264/115
See application file for complete search history.

(56) References Cited

U.S. PATENT DOCUMENTS

| 1,664,631 | A | * | 4/1928 | Koehler ................. C04B 35/06 423/115 |
| 2,502,130 | A | * | 3/1950 | Downs ...................... C09C 1/22 423/430 |
| 4,447,352 | A | | 5/1984 | Inoue et al. |
| 4,462,930 | A | * | 7/1984 | Suzuki ................. G01N 27/121 252/519.1 |
| 4,484,172 | A | | 11/1984 | Grain |
| 4,635,027 | A | | 1/1987 | Miyoshi et al. |
| 5,136,274 | A | | 8/1992 | Shimomura et al. |
| 6,342,295 | B1 | | 1/2002 | Kobayashi |
| 2010/0031745 | A1 | | 2/2010 | Haji-Sheikh et al. |

FOREIGN PATENT DOCUMENTS

| JP | 57-166551 | * 10/1982 |
| JP | 58-168947 | * 10/1983 |
| JP | 58-168950 | * 10/1983 |
| WO | WO 2007/016681 A2 | 2/2007 |

OTHER PUBLICATIONS

Gusmano et al., "Humidity-sensitive electrical response of sintered MgFe2O4" Journal of Material Science, 28 (1993) pp. 6195-6198.*
Shah et al., "Significant increase in humidity sensing characteristics of praseodymium doped magnesium ferrite" Sensors and Actuators, A: Physical (2011), 167(2), pp. 332-337.*

* cited by examiner

*Primary Examiner* — Steven Bos
(74) *Attorney, Agent, or Firm* — Knobbe, Martens, Olson & Bear, LLP

(57) ABSTRACT

The present invention relates to a process for preparing a humidity sensor based on resistive type porous Magnesium Ferrite ($MgFe_2O_4$) pellets and a humidity sensor thereof. More particularly, the present invention includes a synthesis process of preparing 30 to 40% porous $MgFe_2O_4$ pellets. The process further includes making Ohmic contacts on the porous $MgFe_2O_4$ pellets. The process is very cost effective and optimized to keep the resistance of the porous $MgFe_2O_4$ pellets in the range 200-300 M$\Omega$. Further, the response and recovery time of the porous $MgFe_2O_4$ pellets to humidity is in the range of few seconds only. Further, the porous $MgFe_2O_4$ pellets can be used for humidity sensing for more than 12 months. Due to resistance stability even after long-term exposure in humidity, the porous $MgFe_2O_4$ pellets do not require flash heating. Further, the humidity sensor prepared according to the process is highly sensitive towards relative humidity changes as the same is based on the measurement of resistance changes as compared to known humidity sensors which are based on the measurement of capacitance changes.

14 Claims, 4 Drawing Sheets

RESISTIVE TYPE HUMIDITY SENSOR BASED ON POROUS MAGNESIUM FERRITE PELLET

FIELD OF THE INVENTION

The present invention generally relates to humidity sensors. More particularly, the present invention relates to a process for preparing porous Magnesium Ferrite pellets, a process for preparing a resistive type humidity sensor, and a resistive type humidity sensor thereof.

BACKGROUND OF THE INVENTION

Most of known humidity sensors are based on the measurement of capacitance changes. In other words, the sensing of humidity is done by measuring changes in capacitance value. Most of such capacitive type humidity sensors use a porous alumina film or a porous polymer film. Generally, the changes in the capacitance value are not so large. Moreover, the changes are non-linear for a wide range of 10 to 90% relative humidity (RH) change. Further, a complex circuitry is required for detecting the small changes and for linearization of the detected signals. Due to this complex circuitry, response or sensing time is high for the capacitive type humidity sensors. In resistive type known humidity sensors, main problem is to measure high resistance of the order of $G\Omega$ at 10% RH. Porosity is one of the most important parameters for sensing humidity, but it also increases the resistance of the humidity sensor. Thus, such a high resistance limits the sensing range at high 50 to 100% RH. Further, it is also very difficult to develop electronic circuitry to measure such a high resistance.

Patent publication numbered US20100031745 A1 describes a nano porous humidity sensor, and humidity sensing based on change in capacitance. In this sensor, it requires an electrically conductive adhesion layer to produce a robust anodically anodized oxide film on the substrate. All the processing and deposition are done in class-1000 clean room. Further, a disturbance is detected in capacitance of electric current applied across the nano-sensor by a power source. For this purpose, the presence of water vapor in air is detected. The relative humidity of air is determined by analyzing an output electrical signal that is proportional to a concentration of oxidizing or reducing agents on the metal surface of the nano-sensor. The output electrical signal is strongly dependent on the concentration of oxidizing or reducing agents present in air. Thus, accurate detection of water vapor is so critical in any chemical and dusty environment. The detection of concentration of oxidizing or reducing agents present in air is also critically dependent on nano-porous structure of alumina by anodization. All the processing steps of nano-sensor require a class-1000 clean room that adds to the cost of the sensor. The other disadvantage is that the detection capability of the nano-sensor can vary with non-porous distribution. Further, the repeatability of the nano-sensor may vary with time and processing steps.

Patent publication numbered WO2007016681 A2 describes a humidity sensor in for of a deflectable resistor comprising of a substrate and a first layer of a conductive material. Any moisture contacting the surface of the humidity sensor penetrates a number of cracks in a first layer of conductive material. The space between the cracks in the first layer of the conductive material fills with moisture and thereby resistance decreases as the amount of moisture content increases. In another alternative arrangement, the substrate is bendable between a first configuration and a second configuration. The resistance measured between the first end and the second end of an electrically conductive ink layer, which changes by electrical signal applied on it, predictably when layer is bent. The change of resistance of the layer of the conductive ink reflects an amount of deflection between the first configuration and the second configuration. The basic disadvantage of this type of humidity sensor is that moisture content measurement is dependent upon micro-cracks in the conductive material, which can be contaminated easily by dust, smoke and temperature conditions. This can drift the resistance values and may give erroneous results.

U.S. Pat. No. 6,342,295 B1 describes a moisture sensor comprising of a pair of electrodes and a moisture sensitive film deposited between conducting particles dispersed in a hygroscopic polymer. The hygroscopic polymer is a polymer comprising the polyether amine, the epoxy compound, and a water-soluble nylon or a mixture of these polymers that starts to absorb moisture in a humidity region 60% to 90% RH. The disadvantage of such a moisture sensor is polymerization of the polyether amine, the epoxy compound, and the water-soluble nylon is a typical process. Another disadvantage is the amount of conducting particles loading to a critical parameter without which the moisture film loses its sensitivity. The loading of conducting particles in the moisture film is also a typical process. These lengthy and typical synthesis processes make the moisture sensor cost ineffective. In addition, moisture sensitive polymer has limitation towards contamination and thermal stability. Further, the moisture sensitive polymer has a limited range of sensitivity 60 to 90% RH.

U.S. Pat. No. 5,136,274 A describes the detection of relative humidity as a change in electrical resistance using a porous sintered body and electrodes into contact with solution of a polyurethane resin. Further, a durability test of the humidity sensor is conducted. In this durability test various tests, such as water resistance test, oil test, Organic acid test, Inorganic corrosive gas test, cigarette smoke test, and aldehyde test are conducted at fixed 60% relative humidity. The main disadvantage is the variance of base resistance with different porous sintered body compounds. Such a humidity sensor cannot be operated at higher temperatures due to coating of urethane resin.

U.S. Pat. No. 4,635,027 A describes a resistance-variation type moisture sensitive film made essentially of Sodium Styrenesulfonate 100 parts by weight and 3 to 7 parts of polymer. A moisture sensitive film of a polyelectrolyte detects variation of humidity by means of a variation in resistance. The main disadvantage of electrolytic and polymer materials are that they are hydrophilic and soluble in water. Therefore, they have a poor durability against water or dew condensation. Another disadvantage of this moisture sensitive electrolyte is that it is chemically active and unable to operate in the presence of ammonia or organic solvents. Further, thermal stability of this material also restricts its operation at high temperatures.

U.S. Pat. No. 4,484,172 A describes a semiconducting device comprising a humidity sensitive metal oxide coating of lanthanide series cobaltite. An amplifier in conjunction with a humidity detector film is provided that ignites an electric filament lamp or signaling a glow lamp. This device detects changes in resistance from 30 to 100% RH based on film's thickness. The resistance response of the humidity sensor becomes constant after 70% RH which otherwise exhibits its sensitivity between 30 to 70% RH. Another disadvantage is that the detecting film comprised of lanthanide series elements, which makes the product very expensive.

U.S. Pat. No. 4,447,352 A describes the detection of humidity by varying electrical resistance of a humidity sensitive element. The humidity sensitive element consists of 70 to 20% Zinc Ferrite and 30 to 80% a selected group of $MnO_2$ and $SiO_2$, which reduces specific resistance of metal oxide, and thereby detects humidity by changing the electrical resistance. A thin film electrode of Ag, Au, and $RuO_2$, is prepared on both sides of the said material either by printing or by vapor deposition technique. The stability and repeatability data of the humidity sensitive element is not provided. Further, the details of electrode formation technique being typical in nature have not been dealt with. Further, the response time measurement of the humidity sensitive element is also not provided.

OBJECTS OF THE INVENTION

It is an object of the invention to provide a process for preparing a humidity sensor and a humidity sensor thereof which brings large changes in the resistance with variation in RH %.

It is yet another object of the invention to maintain porosity in the range of 30 to 40% without increase in base resistance (<300 MΩ) of material used to prepare the humidity sensor.

It is yet another object of the invention to provide more rugged sensing material which is not affected by corrosive environment and also does not require flash heating.

It is yet another object of the invention to obtain cost effective production and to have stability of resistance response even for long time exposure to humidity.

SUMMARY OF THE INVENTION

In accordance with the purposes of the invention, as embodied and broadly described herein, the invention uses a porous Magnesium Ferrite ($MgFe_2O_4$) pellet for preparing resistive type humidity sensors. The porosity of the porous $MgFe_2O_4$ pellet is maintained between 30 to 40% while keeping the resistance in the range of 200 to 300 MΩ at 10% RH. The porous $MgFe_2O_4$ pellet is easy to process, cost effective unlike porous alumina thin film, and durable. The porous $MgFe_2O_4$ pellet shows a significant change in resistance up to 4 to 8 MΩ for 1% RH change. The response time of the porous $MgFe_2O_4$ pellet is faster than capacitive and other resistive based known humidity sensors. Further, no complicated circuitry is required as compared to capacitive type humidity sensors. Further, the porous $MgFe_2O_4$ pellet is thermally, chemically, and mechanically stable. Further, the porous $MgFe_2O_4$ pellet can be easily calibrated with a simple resistor at specific humidity.

According to one aspect of the invention, a process for preparing porous Magnesium Ferrite pellets having porosity in the range of 30 to 40% comprises: obtaining a homogenous mixture of Magnesium oxide or Magnesium Carbonate and Ferrous oxide in a molar ratio of 1:2; pre-sintering the homogenous mixture in a furnace; grinding the pre-sintered mixture; pelletizing the ground mixture to prepare intermediate pellets; and sintering the intermediate pellets to prepare the porous magnesium ferrite pellets having porosity in the range of 30 to 40%.

According to one aspect of the invention, the grain size of the porous magnesium ferrite pellets is in the range of 50 nm to 1 μm.

According to one aspect of the invention, the pore size of the porous magnesium ferrite pellets is in the range of 15 nm to 450 nm.

According to one aspect of the invention, the pelletizing comprises applying pressure on a predefined amount of the ground mixture through a hydraulic press.

According to one aspect of the invention, the porous Magnesium Ferrite pellets have powder weight 0.1-0.2 g and dimension 5 mm×8 mm×1 mm at applied pressure of 10 tons.

According to one aspect of the invention, the porous Magnesium Ferrite pellets exhibit resistance in the range of 200 to 300 MΩ at 10% relative humidity.

According to one aspect of the invention, the porous Magnesium Ferrite pellets exhibit a change in resistance up to 4 to 8 MΩ for 1% change in relative humidity.

According to one aspect of the invention, resistance value of the porous Magnesium Ferrite pellets is stable at 10%, 50%, and 90% relative humidity.

According to one aspect of the invention, response time and recovery time of the porous Magnesium Ferrite pellets is 120 to 150 seconds and 140 to 200 seconds respectively.

According to one aspect of the invention, a process for preparing a resistive type humidity sensor comprises: obtaining a homogenous mixture of Magnesium oxide or Magnesium Carbonate and Ferrous oxide in a molar ratio of 1:2; pre-sintering the homogenous mixture in a furnace; grinding the pre-sintered mixture; pelletizing the ground mixture to prepare intermediate pellets; sintering the intermediate pellets to prepare the porous magnesium ferrite pellets having porosity in the range of 30 to 40%; and preparing the resistive type humidity sensor using a pellet from amongst the porous magnesium ferrite pellets as base resistive material for the resistive type humidity sensor.

According to one aspect of the invention, the process for preparing a resistive type humidity sensor further comprises: diffusing a group II element added Silver paste on longitudinal edges of the pellet to provide an Ohmic contact at each of the longitudinal edges, wherein the diffusing comprises applying the group II element added Silver paste on longitudinal edges of the pellet and heating the pellet thereafter, and wherein the group II element is Zinc metal; and soldering a TEFLON®, which is a a synthetic fluoropolymer of tetrafluoroethylene, i.e., Polytetrafluoroethylene (PTFE), coated conducting wire on the Ohmic contact at each of the longitudinal edges.

According to one aspect of the invention, the pellet exhibits resistance in the range of 200 to 300 MΩ at 10% relative humidity, and wherein the pellet exhibits a change in resistance up to 4 to 8 MΩ for 1% change in relative humidity.

According to one aspect of the invention, a resistive type humidity sensor comprises: a resistive material sensitive to humidity; and at least two electrodes connected to the resistive material to measure change in resistance of the resistive material, characterized in that a porous Magnesium Ferrite pellet having porosity in the range of 30 to 40% is used as the resistive material.

According to one aspect of the invention, the porous Magnesium Ferrite pellet exhibits resistance in the range of 200 to 300 MΩ at 10% relative humidity.

According to one aspect of the invention, the porous Magnesium Ferrite pellet exhibits a change in resistance up to 4 to 8 MΩ for 1% change in relative humidity.

BRIEF DESCRIPTION OF THE ACCOMPANYING DRAWINGS

To further clarify advantages and features of the invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings in which:

FIGS. 1a, 1b, and 1c illustrate exemplary dimensions of a porous Magnesium Ferrite pellet having soldered electrodes, in accordance with an embodiment of the invention.

Figure 1A:
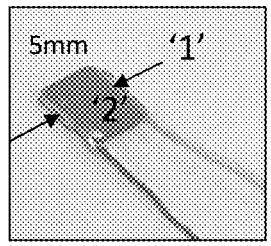

It may be noted that to the extent possible, like reference numerals have been used to represent like elements in the drawings. Further, those of ordinary skill in the art will appreciate that elements in the drawings are illustrated for simplicity and may not have been necessarily drawn to scale. For example, the dimensions of some of the elements in the drawings may be exaggerated relative to other elements to help to improve understanding of aspects of the invention. Furthermore, the one or more elements may have been represented in the drawings by conventional symbols, and the drawings may show only those specific details that are pertinent to understanding the embodiments of the invention so as not to obscure the drawings with details that will be readily apparent to those of ordinary skill in the art having benefit of the description herein.

DETAILED DESCRIPTION

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof. Throughout the patent specification, a convention employed is that in the appended drawings, like numerals denote like components.

Reference throughout this specification to "an embodiment", "another embodiment" or similar language means that a particular feature, structure, or characteristic described in connection with the embodiment is included in at least one embodiment of the invention. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures proceeded by "comprises . . . a" does not, without more constraints, preclude the existence of other devices or other sub-systems.

In present invention, a synthesis process for preparation of porous $MgFe_2O_4$ pellets for humidity sensing and a humidity sensor thereof is described. The porous $MgFe_2O_4$ pellets are capable of exhibiting a two order drop in resistance with increase in humidity. Embodiments of the present invention will be described below in detail with reference to the accompanying drawings.

Figure 1B:
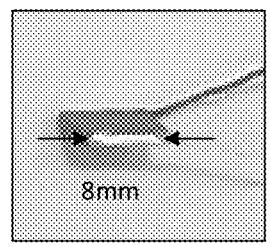
Figure 1C:
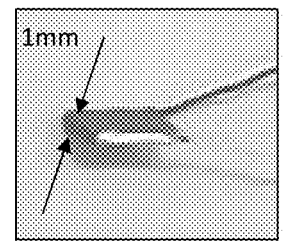

FIGS. 1a, 1b, and 1c illustrate a synthesized (5 mm×8 mm×1 mm) porous Magnesium Ferrite ($MgFe_2O_4$) pellet with a surface '2' having maximum area exposed to humidity. Said figures also depict soldered wires or electrodes '1' on Ohmic electro-conducting silver electrode area of the porous $MgFe_2O_4$ pellet. These Ohmic contacts may be prepared by curing the group II elements added silver-pasted pellets. Further, TEFLON® coated conducting wires may be soldered on the Ohmic contacts to make a mechanically and electrically stable connection. Any change in the resistance of the porous $MgFe_2O_4$ pellet may be measured across these wires.

Figure 2:
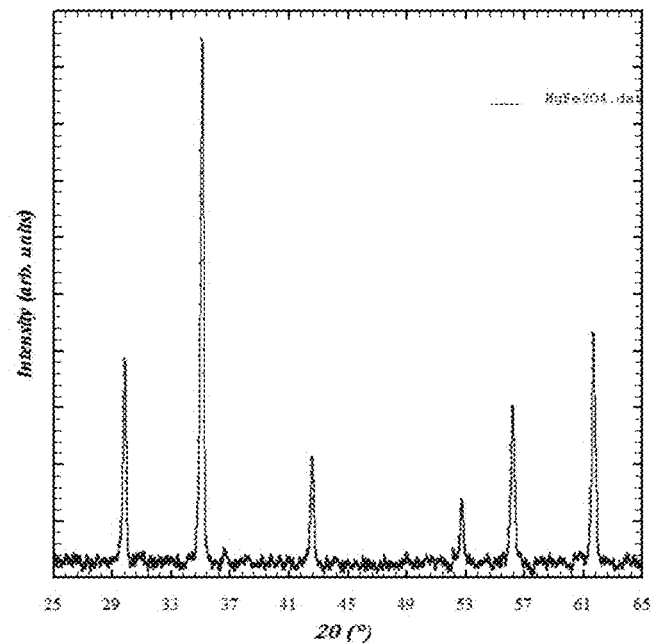
FIG. 2 illustrates an X-ray diffraction pattern of the porous Magnesium Ferrite pellet, in accordance with an embodiment of the invention.

FIG. 2 illustrates an X-ray diffraction pattern of the porous $MgFe_2O_4$ pellet exhibiting single phase formation of the compound. As shown in the X-ray diffraction pattern, all peaks are coinciding with spinel peaks of spinel ferrite. The biggest difficulty in synthesizing $MgFe_2O_4$ has been in the control of the stoichiometry. $MgFe_2O_4$ may depart from the perfect stoichiometric in three directions: (1) Substitution of $Fe^{2+}$ for Mg, causing solid solution toward $Fe_3O_4$; (2) Solid solution toward $\alpha\text{-}Fe_2O_3$, (maghemite); and (3) Excess MgO. The first two mechanisms are well established possibilities under certain conditions. However, evidence for the importance of the last one is equivocal. Nominally stoichiometric $MgFe_2O_4$ may partially decompose to a $Fe_3O_4$ containing solid solution according to the reaction: $6MgFe_2O_{4-x}4Fe_3O_4+6MgO+O_2$. At constant $O_2$ pressure, such as that of air, above reaction goes progressively more to the right side with increasing temperature. It should only be possible to synthesize something approaching stoichiometric $MgFe_2O_4$ at relatively low temperatures, at least in air for $Fe_3O_4$ to be below 0.5%. The synthesis temperatures should be less than 1050° C.

Figure 3:
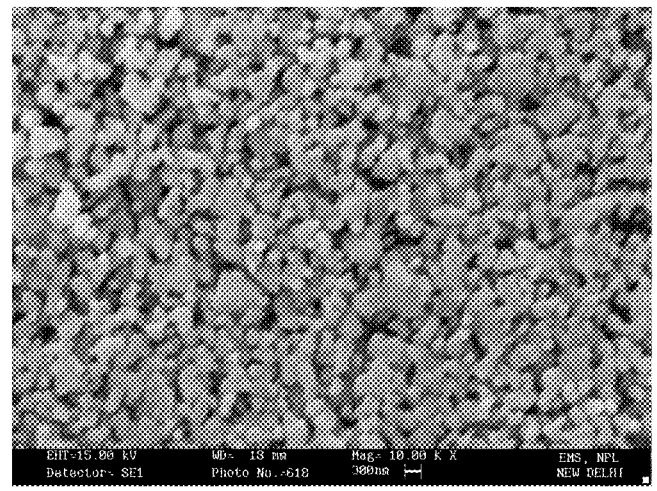
FIG. 3 illustrates a scanning electron micrograph indicating porous morphology of the porous Magnesium Ferrite pellet, in accordance with an embodiment of the invention.

FIG. 3 illustrates a scanning electron micrograph indicating porous morphology of the porous $MgFe_2O_4$ pellet. As shown, the porous microstructure of the porous $MgFe_2O_4$ pellet has distribution of wide range pore sizes, ranging from micro to macro size. The grain size distribution may be calculated by applying linear intercept method on SEM micrographs of magnesium ferrite pellet. The grain and the pore size distribution may be in the range of 50 nm to 1 μm and 15 nm to 450 nm respectively. A combination of meso (2 nm to 50 nm) and macropores (>50 nm) are connected through grain neck over the entire surface of the porous $MgFe_2O_4$ pellet and are visible in SEM micrograph. Micropores (<2 nm) may be present within the grain, but are not visible in SEM resolution range.

Figure 4:
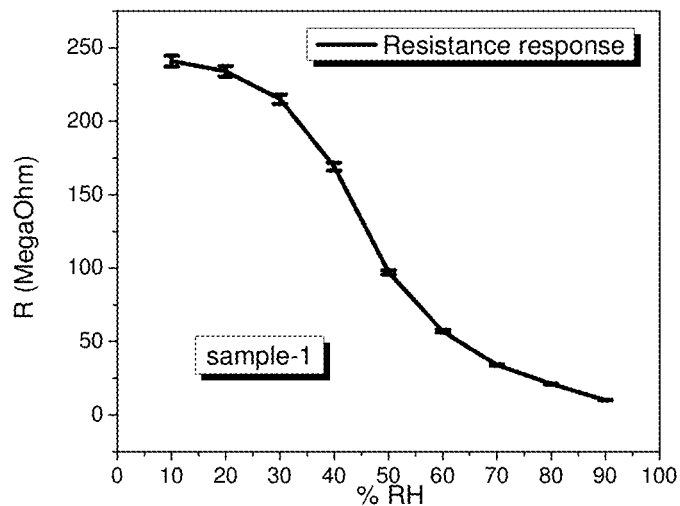
FIG. 4 illustrates a plot of resistance response of the porous Magnesium Ferrite pellet, in accordance with an embodiment of the invention.
Figure 5:
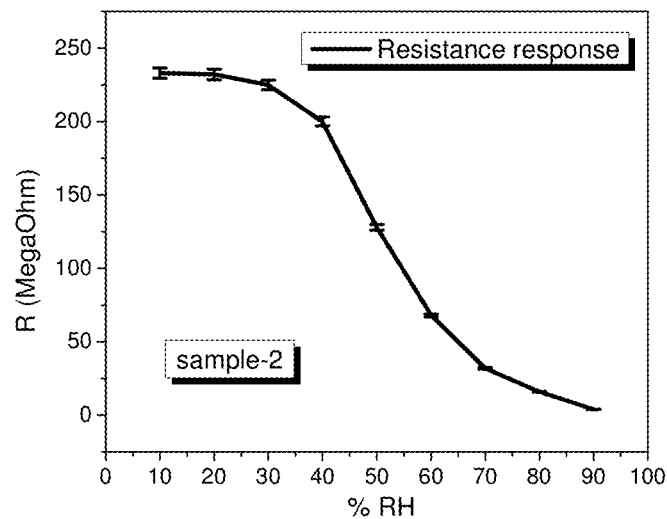
FIG. 5 illustrates a humidity response curve of the porous Magnesium Ferrite pellet, in accordance with an embodiment of the invention.

FIGS. 4 and 5 illustrate the change in resistance of sample 1 and sample 2 with relative humidity. More particularly, FIG. 4 is the plot of resistance response of sample 1 with change in humidity from 10 to 90% RH range, while FIG. 5 shows the humidity response curve for sample 2 with change in humidity from 10 to 90% RH range. At lower humidity from 10 to 30% RH the decrease in resistance is not so sharp as it may be due to less physisorbed water vapor layer formation and feeble connectivity among few physisorbed water vapor layers. Between 30-70% RH a sharp linear drop in resistance exhibited by the samples 1 and 2. In this humidity range, appropriate pore size distribution is available for adsorption as well as connectivity in physisorbed layers. Above 70% RH resistance value, it shows saturation tendency for water vapor adsorption. Appropriate pore size distribution for wide range humidity sensing by the sample strongly depends upon the sintering temperature and time of the magnesium ferrite sample. If sample is sintered below 1050° C. a great undesirable humidity hysteresis appears as a result of the repeated water vapor adsorption & desorption due to the presence of more defective structure. If sintering temperature is higher than 1050° C., the resistance response of Magnesium Ferrite with humidity deviates from linearity as density of the sample improves. If sintering time is above 4 to 6 hours, some micro-pores get closed and low humidity sensitivity becomes unresponsive. If sintering time is below 4 to 6 hours, the mechanical strength of the sample is weakened and it easily gets broken.

Figure 6:
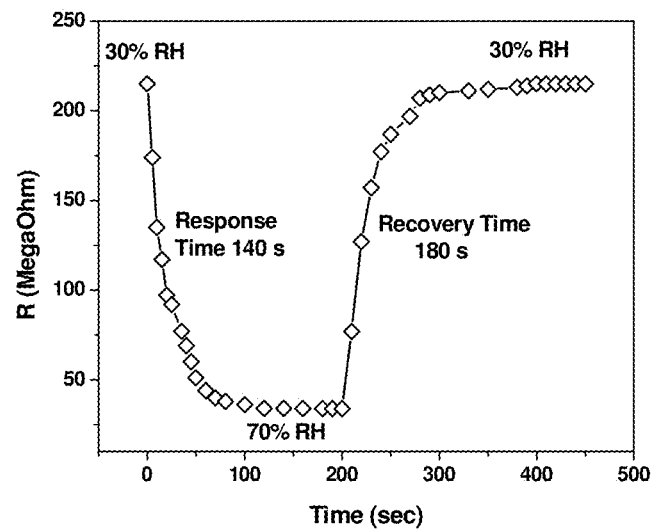
FIG. 6 illustrates another humidity response curve of the porous Magnesium Ferrite pellet, in accordance with an embodiment of the invention.

FIG. 6 illustrates the determination of response and recovery time. For any sensing material, the response time is considered as an important parameter for sensing property of a material. Time taken by the sample to attain 90% resistance value at 70% RH from base value when changed from 30% RH is the adsorption time and reverse is desorption time for that range. The adsorption time is observed as 140 seconds for 30 to 70% RH change and desorption time 180 seconds for 70 to 30% RH change for porous Magnesium Ferrite pellet.

Figure 7:
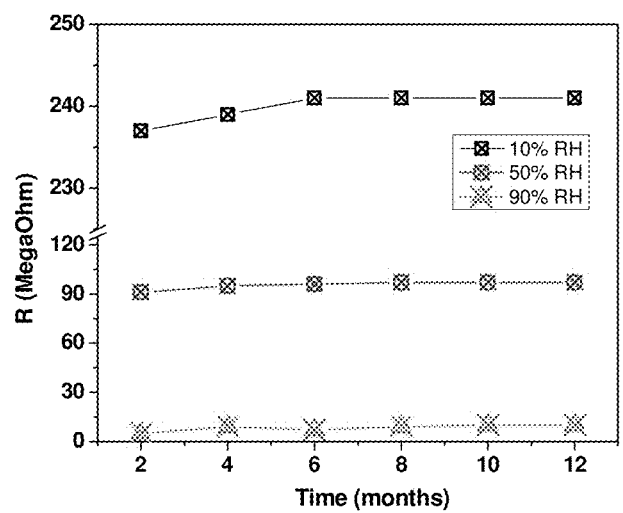
FIG. 7 illustrates a plot of resistance stability of the porous Magnesium Ferrite pellet, in accordance with an embodiment of the invention.

FIG. 7 illustrates the stability of the resistance response of the sample, which may be determined with respect of time, say 12 months, at 10%, 50%, and 90% RH. As shown, drift in resistance of the sample with respect to time in 12 months at specific humidity is approximately 2 to 3%.

The method of preparing the porous porous $MgFe_2O_4$ pellet is described below with help of following examples:

Example 1

MgO (purity 99.9%) and $Fe_2O_3$ (99%) are mixed in molar ratio 1:2. Powder of the two oxides is ground in a pestle with mortar for 1 hour to make them fine and homogenized. Ground powder mixture is kept in to a furnace in air at 800 to 900° C. for 8 to 10 hours at the rate of 5° C./min. Presintered powder is again ground for 1 hour. Further, 0.1 to 0.2 grams powder is weighed for making various pellets. Rectangular pellets of a suitable size, say 5 mm×8 mm×1 mm, are formed from the powder. The pressure applied by a hydraulic press may be 10 Ton for 2 minutes. Several uniform pellets of 0.1 to 0.2 grams are kept for sintering at 950 to 1050° C. for 4 to 6 hours in air at the rate of 5° C./min. Zinc metal added silver paste is applied on longitudinal edge, i.e., along the 5 mm length, of the rectangular pellets. The silver pasted pellets are kept at 300 to 350° C. for 15 to 20 minutes so that silver paste gets diffused inside the porous material and group II element reduces the band gap between electrodes and semiconductor magnesium ferrite for making Ohmic contacts. TEFLON® coated conducting wires are soldered on silver coated side. As shown in FIG. 1*a*, a surface '2' having maximum area is exposed to humidity resulting in to resistance variation type humidity sensor. The resistance of the pellet may be $243 \times 10^6 \Omega$ at 10% RH at 25° C.

Example 2

$MgCO_3$ having 99.9% purity and $Fe_2O_3$ having 99% purity are mixed in molar ratio 1:2. Mixture of the two is ground in a pestle with mortar for 1 hour to make them fine and homogenized. Ground powder mixture is kept into a furnace in air at 800 to 900° C. for 8 to 10 hours at the rate of 5° C./min. During presintering, temperature may be held at 500 to 530° C. for 1 hour to decompose $MgCO_3$ into MgO and $CO_2$. The presintered powder is again ground for 1 hour. Further, 0.1 to 0.2 grams powder is weighed for making various pellets. Rectangular pellets of a suitable size, say 5 mm×8 mm×1 mm, are formed from the presintered powder. The pressure applied by hydraulic press may be 10 Ton for 2 to 5 minutes. Several uniform pellets of 0.1 to 0.2 grams are kept for sintering at 950 to 1050° C. for 8 to 10 hours in air at the rate of 5° C./min. Zinc metal added silver paste is applied on longitudinal edge, i.e., along 5 mm length, of the rectangular pellets. The silver pasted pellets are kept at 300 to 350° C. for 15 to 20 minutes so that silver paste gets diffused inside the porous material and group II element reduces the band gap between electrodes and semiconductor magnesium ferrite for making Ohmic contacts. TEFLON® coated conducting wires are soldered on silver coated side. As shown in FIG. 1*a*, a surface '2' having maximum area is exposed to humidity resulting in to resistance variation type humidity sensor. The resistance of the pellet may be $285 \times 10^6 \Omega$ at 10% RH at 25° C.

The main advantages of the present invention are as follows. It provides a simple and easy synthesis process. Basic materials used, i.e., oxide materials $Fe_2O_3$ and MgO, are low cost material. Due to resistance changes, the response time is faster than capacitive type humidity sensor. Electronic circuitry to measure resistance change is very simple giving very high precision at low cost. Flash heating is not required for regeneration. Owing to low cost, the humidity sensor as per the present invention is easily replaceable. Further, the humidity sensor as per the present invention can be calibrated by a simple resistor at specific humidity.

While certain present preferred embodiments of the invention have been illustrated and described herein, it is to be understood that the invention is not limited thereto, but may be otherwise variously embodied and practiced within the scope of the following claims.

What is claimed is:

1. A process for preparing porous magnesium ferrite pellets having porosity in the range of 30 to 40%, the process comprising:
   obtaining a homogenous mixture of magnesium oxide or magnesium carbonate and ferrous oxide in a molar ratio of 1:2;
   pre-sintering the homogenous mixture in a furnace;
   grinding the pre-sintered mixture;
   pelletizing the grounded mixture to prepare intermediate pellets; and
   sintering the intermediate pellets to prepare the porous magnesium ferrite pellets having porosity in the range of 30 to 40%.

2. The process as claimed in claim 1, wherein the grain size of the porous magnesium ferrite pellets is in the range of 50 nm to 1 μm.

3. The process as claimed in claim 1, wherein the pore size of the porous magnesium ferrite pellets is in the range of 15 nm to 450 nm.

4. The process as claimed in claim 1, wherein the pelletizing comprises applying pressure on a predefined amount of the ground mixture through a hydraulic press.

5. The process as claimed in claim 3, wherein the porous magnesium ferrite pellets have powder weight 0.1-0.2 g and dimension 5 mm×8 mm×1 mm at applied pressure of 10 tons.

6. The process as claimed in claim 1, wherein the porous magnesium ferrite pellets exhibit resistance in the range of 200 to 300 MΩ at 10% relative humidity.

7. The process as claimed in claim 1, wherein the porous magnesium ferrite pellets exhibit a change in resistance up to 4 to 8 MΩ for 1% change in relative humidity.

8. The process as claimed in claim 1, wherein resistance value of the porous magnesium ferrite pellets is stable at 10%, 50%, and 90% relative humidity.

9. The process as claimed in claim 1, wherein response time and recovery time of the porous magnesium ferrite pellets is 120 to 150 seconds and 140 to 200 seconds respectively.

10. A process for preparing a resistive humidity sensor, the process comprising:
   obtaining a homogenous mixture of magnesium oxide or magnesium carbonate and ferrous oxide in a molar ratio of 1:2;
   pre-sintering the homogenous mixture in a furnace;
   grinding the pre-sintered mixture;
   pelletizing the grounded mixture to prepare intermediate pellets;
   sintering the intermediate pellets to prepare the porous magnesium ferrite pellets having porosity in the range of 30 to 40%; and
   preparing the resistive type humidity sensor using a pellet from amongst the porous magnesium ferrite pellets as base resistive material for the resistive humidity sensor.

11. The process as claimed in claim 10, further comprising:
   diffusing a group II element added silver paste on longitudinal edges of the pellet to provide an ohmic contact at each of the longitudinal edges, wherein the diffusing comprises applying the group II element added silver paste on longitudinal edges of the pellet and heating the pellet thereafter, and wherein the group II element is zinc metal; and
   soldering a polytetrafluoroethylene coated conducting wire on the Ohmic contact at each of the longitudinal edges.

12. The process as claimed in claim 10, wherein the pellet exhibits resistance in the range of 200 to 300 MΩ at 10% relative humidity, and wherein the pellet exhibits a change in resistance up to 4 to 8 MΩ for 1% change in relative humidity.

13. A resistive humidity sensor comprising:
   a resistive material sensitive to humidity; and
   at least two electrodes connected to the resistive material to measure change in resistance of the resistive material, wherein the resistive material is a porous magnesium ferrite pellet having porosity in the range of 30 to 40%, the electrodes are soldered on an ohmic electro-conducting silver electrode area of said porous magnesium ferrite pellet, and wherein said pellet exhibits a resistance in the range of 200 to 300 MΩ at 10% relative humidity.

14. The resistive type humidity sensor as claimed in claim 13, wherein the porous magnesium ferrite pellet exhibits a change in resistance up to 4 to 8 MΩ for 1% change in relative humidity.

* * * * *